United States Patent [19]
Williams et al.

[11] Patent Number: 5,749,850
[45] Date of Patent: May 12, 1998

[54] BREAST PUMP

[75] Inventors: Roger Leonard Williams, Herts; David Anthony Edgerley, London, both of United Kingdom

[73] Assignee: Cannon Rubber Limited, London, England

[21] Appl. No.: 619,171

[22] Filed: Mar. 21, 1996

[30] Foreign Application Priority Data

Mar. 24, 1995 [GB] United Kingdom .................. 9506014

[51] Int. Cl.⁶ ..................................................... A61M 1/06
[52] U.S. Cl. ........................................... 604/74; 604/320
[58] Field of Search ................................. 604/74, 75, 76, 604/320, 73, 315

[56] References Cited

U.S. PATENT DOCUMENTS 4,772,262 9/1988 Grant et al. .
4,813,932 3/1989 Hobbs ................................. 604/74
5,071,403 12/1991 Larsson ................................. 604/74

FOREIGN PATENT DOCUMENTS

2658322 12/1976 Germany .
2166353 9/1985 United Kingdom .
9502995 2/1995 United Kingdom .

Primary Examiner—Michael Buiz
Assistant Examiner—Kevin Truong
Attorney, Agent, or Firm—Lowe, Price, LeBlanc & Becker

[57] ABSTRACT

A breast pump is disclosed comprising a body (50) with an inlet (84) thereto to receive milk expressed from a woman's breast. The body is formed for releasable attachment to a container for collecting expressed milk and houses a deformable diaphragm (51) which is cyclicly moved by manually or electrically driven actuating lever (53, 54) connected thereto to generate and release cyclicly a negative pressure in the nipple region sufficient to stimulate the nipple area to cause lactation. The pump preferably includes valve (80) mounted in the body so that the negative pressure is created in the pump body only and not in the container for the expressed milk when connected thereto.

21 Claims, 5 Drawing Sheets

BREAST PUMP

BACKGROUND OF THE INVENTION

This invention relates to a breast pump which can either be manually operated or electrically driven.

1. Field of the Invention

Electric pumps are known but they tend to be complicated in construction and not particularly convenient to use. An example of Such a pump can be found in U.S. Pat. No. 4,772,262.

2. Description of the Relevant Art

The applicants improved on the electric pump described in U.S. Pat. No. 4,772,252 and developed a manually operated single handed breast pump which is described and claimed in their British Patent No. 2166353. This pump comprises a body including a breast and nipple receiving part and a base part enabling the connection thereto of a container to collect expressed milk. The body houses manually operable means to create a negative pressure at the nipple sufficient to express milk therefrom, said means including a valve system operable to pressurize the volume in the body but not the volume in the milk collecting container when connected to the base part. The pump is constructed and arranged so that it can be held against the breast and nipple by the user with one hand only, said same hand being used to manually operate the lever connected to a piston which reciprocates in a barrel located in the body to create the negative pressure at the nipple. Whilst this pump provided a considerable improvement over prior art pumps due to its simplicity of construction and single handed usability, it was found in practice that the negative pressure it generated could leak past the seal between the piston and the barrel on each stroke. This problem could be solved by designing the seal to apply a greater pressure against the barrel walls but this was found to be disadvantageous because it increased the friction therebetween thereby necessitating a stronger return spring which made the pump harder to use and could prove tiring for the user. Furthermore, the pump assembly as a whole was made up from a large number of parts which reduced its convenience of assembly and stripping down for cleaning and/or sterilization purposes.

SUMMARY OF THE INVENTION

It is an object of the present invention therefore to provide an improved pump which is easier and more convenient to use and simpler to strip down for cleaning and reassembly.

According to the invention there is provided a breast pump comprising a body with an inlet thereto to receive milk expressed from a woman's breast, means for releasably attaching the pump to a container for collecting expressed milk, the body housing a deformable diaphragm which, in use, is cyclicly moved by actuating means connected thereto to generate and release cyclicly a negative pressure in the nipple region sufficient to stimulate the nipple area to cause lactation therefrom.

Preferably, valve means are located in the body so that said negative pressure is created in the pump body only and not in the container for the expressed milk when connected thereto.

The actuating means may be manually or electrically moved to distort the diaphragm and create said negative pressure.

The actuating means may be directly connected to the diaphragm or a separate connector may be fitted thereto.

In one embodiment, the actuating means includes a lever which has a handle portion and a nose portion, the handle portion being pivotally mounted on the body and the nose portion engaging with the diaphragm, the arrangement being such that the handle moves relative to the body in a direction generally normal thereto as a result at which the nose portion moves axially of the body.

Preferably the connector comprises a projection which extends upwardly from the diaphragm for engagement by the actuator means.

Preferably, the diaphragm is cup-shaped and the connector is a post which extends upwardly from the base thereof. The post can be integrally formed with the diaphragm but it is preferably a separate component which is releasably fitted thereto.

The diaphragm is releasably retained in the body. In one embodiment, this is achieved using a retaining member or holder which fits into the body to hold the diaphragm in position whereby it makes a fluidtight seal therewith.

In another embodiment, the body has an upstanding annular lip which is received in all annular rebate formed around the circumference of the diaphragm, the retaining member holding the diaphragm in sealing engagement therewith.

Conveniently, the retaining member is a cover which fits on the top of the body to enclose the diaphragm, said cover having an annular sealing surface which engages with the outer surface of the diaphragm to hold it in sealing engagement with the annular lip on the body.

Preferably, the cover included retaining means to hold said cover n position on the body. Conveniently, said retaining means comprise resilient tabs on the cover which engage with projections extending from the body.

Preferably, the lever includes a handle portion and the holder has a pivot support projecting therefrom which pivotally mounts the lever handle thereon. Suitably, the nose portion of the lever includes a connection means releasably connecting the lever to either directly or indirectly to the diaphragm. In the preferred embodiment, the connection means comprises a forked end on the nose portion of the lever which engages with a connector protruding from the diaphragm. Conveniently, the connector has an enlarged head portion provided at one end thereon which is engaged by said forked end of the lever. The lever can however have a hole in its nose portion to receive said enlarged head on the connector. The lever can be moved against the action of a spring located between the connector and a cover fitted to the top of the pump to enclose the nose portion of the lever but preferably no spring is used and instead the resilience of the diaphragm provides the return biasing force assisted by atmospheric pressure.

The valve means preferably comprises a valve fitted in an aperture in a wall extending across the body adjacent where it is attached to the milk collecting container.

Conveniently, the body includes a moulded portion provided with threads to enable it to be screwed directly to a milk collecting container such as a plastic bottle of known type but it can be mounted on the container in any convenient known way. An the neck portions of known plastic bottles vary in diameter, rather than producing a pump with different threaded portions in the base thereof to fit each different bottle neck size, it is envisaged within the scope of the invention to provide the base of the pump body with releasable connecting means for attaching it to an adaptor which itself is configured to fit various different bottle neck diameters with such an arrangement, the adaptor can first be fitted to the bottle and the pump body can then be attached to the adaptor, for instance using a bayonet fitting or some other known releasable connection arrangement. A convenient way of attaching the adaptor to the bottle would be to provide the tubular body of the adaptor with an outwardly extending annular flange which can be sandwiched between the upper rim of the bottle and the screw cap normally used to attach the teat to the bottle, the body of the adaptor extending through a central hole in the screw cap.

It is also envisaged within the scope of the invention to omit the hand lever and replace it with a modified actuator assembly connected to an electrically operated drive mechanism. In such a pump, the electric drive mechanism would preferably include a step-down arrangement whereby the diaphragm is moved cyclicly at one cycle every 1–2 seconds rather than continuously at 30–60 cycles per second which would he the normal operating rate of the electric motor.

Two preferred pumps of the present invention will now be described, by way of example only, with reference to the accompanying drawings in which.

BRIEF DESCRIPTION OF THE DRAWINGS

DETAILED DESCRIPTION OF THE PREFERRED EMBODIMENTS

Figure 1:
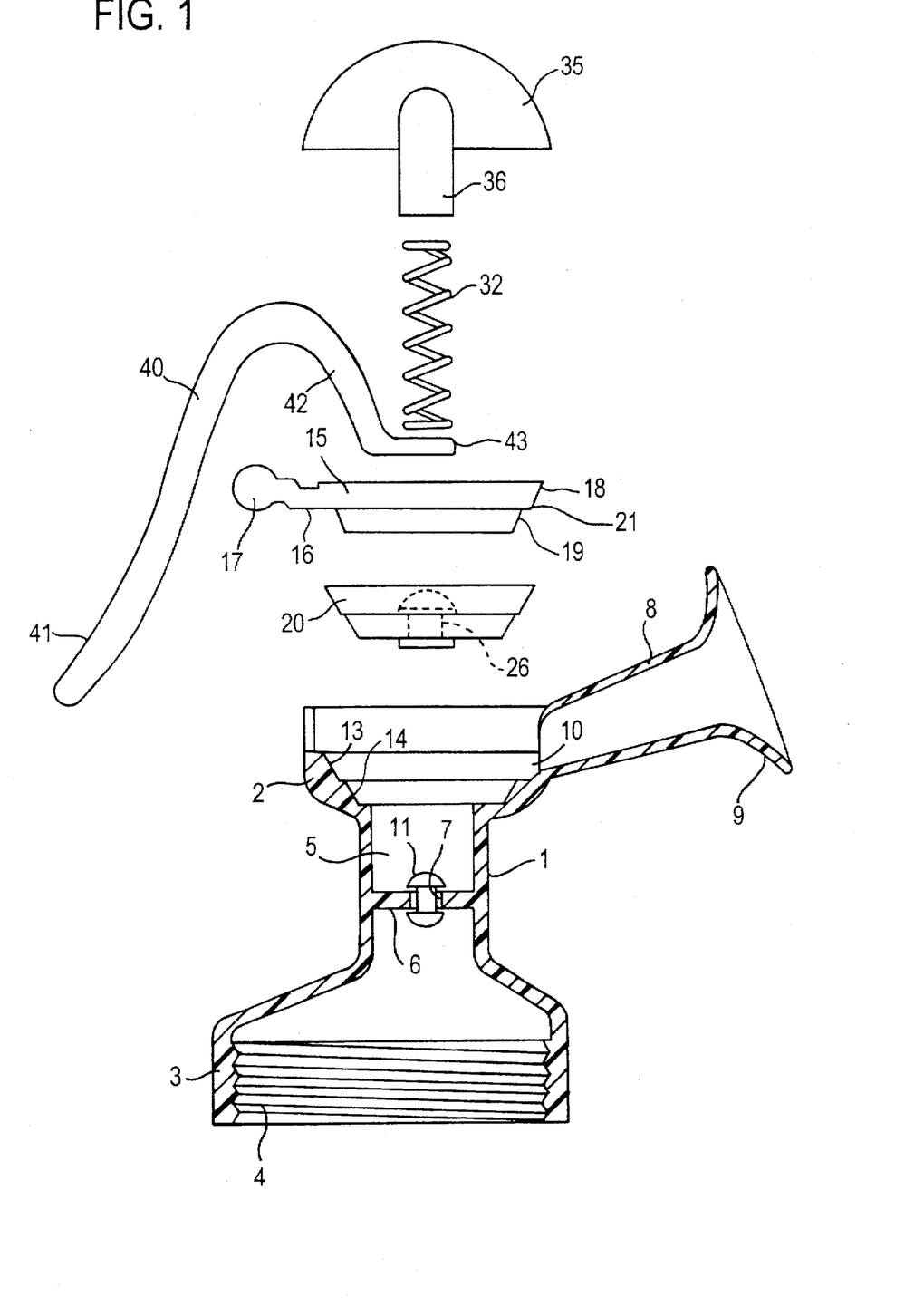
FIG. 1 is an exploded view of the components of a first pump of the invention.
Figure 2:
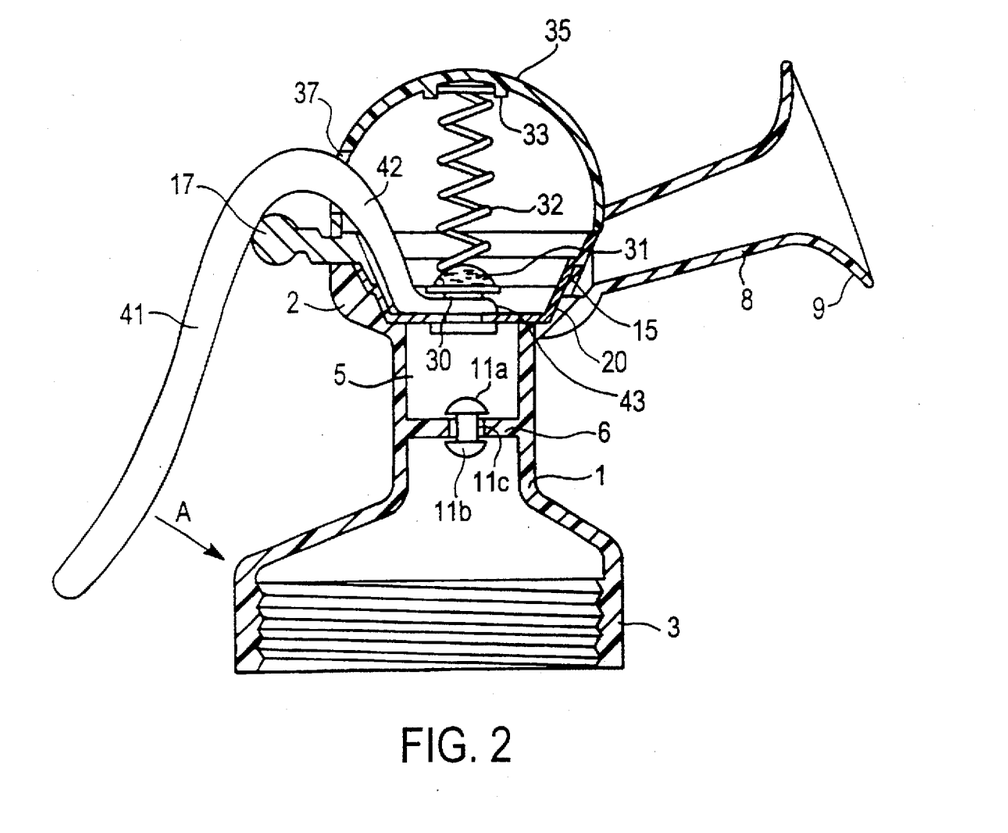
FIG. 2 shows the pump of FIG. 1 in its assembled state.

Referring to the drawings and in particular to FIGS. 1 and 2, there is shown a single handed breast pump comprising a moulded plastics body 1 including a cup-shaped upper portion 2 and a lower portion 3 with threads formed on the internal surface thereof so that the body can be screwed onto a milk collecting vessel (not shown) e.g. a baby feed bottle or some other suitable container. The body includes an internal dividing wall 6 which separates the cup-shaped upper portion 2 from the lower portion 3 and is formed with a central hole 7 in which a plug valve 11 is mounted. The valve 11 comprises end portions 11a and 11b (see FIG. 2) connected by a central section 11c whose length is greater than the thickness of the dividing wall 6 so that the plug valve 11 can move axially in the hole 7 by the distance separating the end sections 11a and 11b thereof. The reason for this axial movement will be described hereafter.

An inlet trumpet 8 is formed at one side of the cup-shaped upper section 2 of the body 1 and its free end is enlarged to provide a conical section 9 shaped to receive the breast and nipple of a user. An inlet opening 10 (see FIG. 1) is formed in the upper cup-shaped section 2 to place the interior of the body 1 in communication with the inlet trumpet 8. The interior surface of the cup-shaped section 2 is moulded to include two contoured surfaces 13 and 14 (see FIG. 1) the purpose of which will be described shortly.

Figure 5:
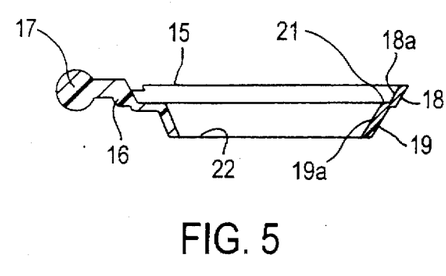
FIG. 5 is a cross section of the diaphragm retainer member shown in FIGS. 1–3.
Figure 5A:
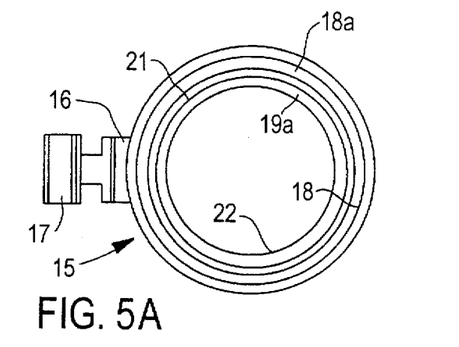
FIG. 5A is a plan view of the diaphragm retainer shown in FIG. 5.

Referring now to FIGS. 1 and 5, there is shown a circular moulded rigid plastics diaphragm holder 15 having an upper section 18 of a first diameter and a lower section 19 of a second diameter connected by an intermediate step section 21. It will be noted that the cross sectional shape of the holder 15 is generally frusto conical. The bottom edge of the lower section 19 defines a central aperture 22. An extension 16 extends laterally from one side of the holder 15 and has a hinge pivot 17 formed at one end thereof. The external contours of the holder 15 and in particular the contours of the upper and lower sections 18 and 19 are shaped so that they fit exactly inside the diaphragm 20 and hold it against surfaces 13 and 14 of the cup-shape portion 2 of the body 1 to make a fluid tight seal therewith.

Figure 4:
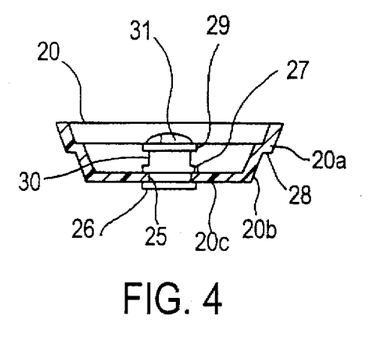
FIG. 4 is a cross section of the diaphragm shown in FIGS. 1–3.
Figure 4A:
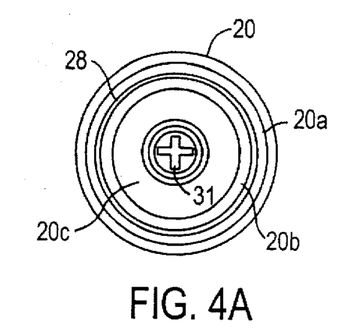
FIG. 4A is a plan view of the diaphragm shown in FIG. 4.

Referring now to FIGS. 4 and 4A, there is shown a cup-shaped diaphragm 20 which comprises an upper section 20a connected to a lower section 20b by means of a stepped portion 28. The diaphragm 20 also includes a radially inwardly extending bottom wall 20c extending from the lower wall 20 and having a central aperture 25 formed therein. A moulded plastics stem connector 26 is formed with a bottom annular rebate 27 therein which mounts the connector 26 in the hole 25. The connector 26 is also formed with an upper annular rebate 30 the purpose of which will be described shortly. The upper part 29 of the stem connector has moulded thereon an upstanding projection 31 which serves to locate a spring 32 (see FIGS. 1 and 2).

Figure 6:
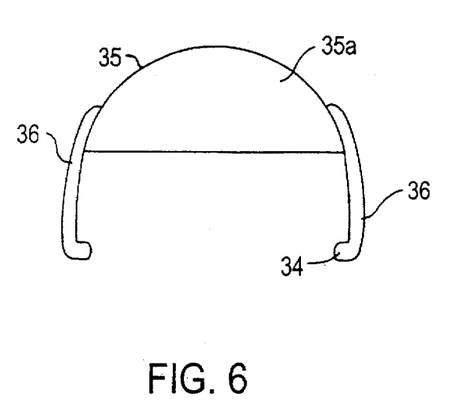
FIG. 6 is a side view of the cap or cover shown in FIGS. 1–3.
Figure 6A:
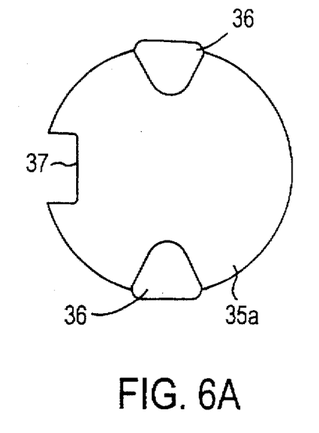
FIG. 6A is a plan view of the cap or cover shown in FIG. 6.

Referring now to FIGS. 6 and 6A, there is shown a cap 35 which comprises a part spherical cover portion 35a having a pair of downwardly extending legs 36 attached thereto at locations diametrically opposite each other. The free end of each leg 36 includes an inwardly directed lip 37 to engage with the body 2 and retain the cap 35 thereon. As can be seen more clearly in FIG. 6A, a cut-out portion 37 is provided on one side of the cap 35 to provide access for lever 40.

Figure 3:
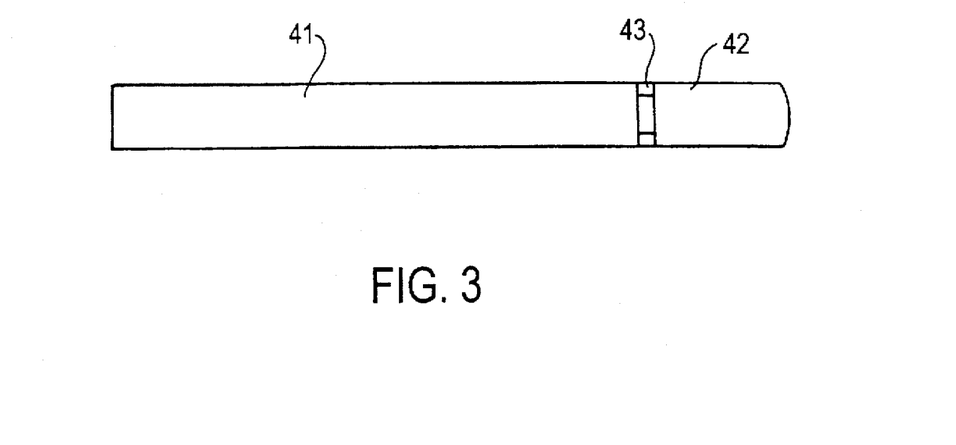
FIG. 3 is a plan view of the lever shown in FIGS. 1 and 2.

The moulded plastics lever 40 is illustrated in more detail in FIGS. 1–3 and comprises a handle 41 connected to a nose portion 42 having a forked end 43 defining a gap 44 therein (see FIG. 3).

FIG. 1 illustrates the various components of the breast pump of the present invention in their unassembled condition whereas FIG. 2 shows them in their assembled condition. It can be seen that the diaphragm 20 is mounted directly in the body 2 and the holder 15 is then fitted into the cup-shaped portion 2 of the body 1 to hold the diaphragm in position whereby it makes a fluidtight seal with the annular surfaces 13 and 14 of the body 2. The connector 26 is mounted in the central aperture 25 in the diaphragm and extends upwardly therefrom. The handle 41 is mounted relative to the cup-shaped portion 2 so that its forked nose 43 locates in the rebate 30 under the top part 29 of the stem connector 26.

The cap 35 is attached to the upper region of the cup-shaped body portion 2 and retained in position thereon by means of the downwardly depending legs 36 whose ends 37 engage with suitably recesses (not shown) formed on the body 1.

A coil spring 32 is mounted on the spring locating means 31 on the top 29 of the actuator. The inside surface of the cover 35 is formed with an annular wall 33 (see FIG. 2) to provide a locating recess on the undersurface of the cap 35 to receive the other end of the spring 32. Thus, the spring 32 acts between the cover 35 and the forked nose 43 of the lever 41 to bias the lever 41 into its rest position shown in FIG. 2. The lever 41 extends from the interior of the body 1 to the exterior thereof through the gap 37 provided in the cover 35.

The use and operation of the illustrated pump is as follows. First of all, the lower portion 33 is screwed on to a suitable milk collecting container (not shown) such as a baby bottle of known type and the pump is now ready to use. The user first inserts her breast and nipple into the conical portion 9 at the end of the inlet trumpet 8 and holds the body 1 with the milk collecting container (not shown) connected thereto against her breast. Due to the design of the breast pump, she is able to place her thumb around the barrel portion 1 of the body and her fingers over the handle 41. She can then apply pressure to the handle 41 to move it in the direction of arrow A (see FIG. 2) which is generally laterally with respect to the body 1 and towards her breast. This results in the handle 41 pivoting about the pivot 17 and raising the nose portion 42 which lifts the connector 26 and distorts the diaphragm 20 connected thereto. This creates a negative pressure in the chamber 5 and plug valve 11 is immediately lifted upwardly thereby causing the plug valve section 11b to seat against the lower surface of the dividing wall 6 to form a seal therewith. As a result, the negative pressure is maintained while the lever 41 is being moved towards the body of the breast pump and until its stroke is completed. This negative pressure created in the region 5 between the valve 11, the diaphragm 20 and the users breast in the conical portion 9 is sufficient to cause the breast to lactate and milk to be expressed therefrom.

On release of the pressure on the handle 41 by the user, the spring 32 acting between the cover 35 and the forked nose 43 of the handle 41 which is now compressed expands and returns the handle to its rest position illustrated in FIG. 2. As a result, the diaphragm 20 returns to its original configuration shown in FIG. 2 thereby creating a positive pressure which allows the plug valve 11 to break its seal with the dividing wall 6 and the milk expressed from the breast contained in the area 5 to fall under gravity into the milk collecting container (not shown) attached to the lower portion 3 of the breast pump body 1.

The cycle is then repeated.

Lactation generally results if a vacuum is created in the region of the nipple but the flow can be improved if the breast itself is stimulated in some way. Lactation is best promoted if an alternating pressure is created in the nipple region in a cyclic fashion. In other words, it is preferable to create a negative pressure initially and then reduce or release it preferably by venting to atmosphere and the pump just described operates in this way.

Whilst it is preferred that return spring 32 is used, the diaphragm 20 could be moulded of a material which is sufficiently resilient to ensure that the lever 41 returns to its rest position shown in FIG. 2 on release of the pressure thereon using the natural resilience of the diaphragm itself and the effects of atmospheric pressure. It will be appreciated that the force required to overcome the resilience of the diaphragm 20 to deform and raise it will be less when the return spring is omitted so a shorter handle 41 can be used. This not only saves space and materials but it makes the pump much easier to use. For instance experiments have shown that as much as between 5 and 10 times less pressure is needed to raise the diaphragm than is the case when a return spring is used.

The preferred embodiment just described with reference to FIGS. 1–6 of the drawings is manually operated. It is however envisaged within the scope of the invention that the lever 41 can be replaced by a modified actuator assembly which can be reciprocated by a motorised drive mechanism connected thereto to deform the diaphragm and create the negative pressure in the chamber 5 in the body 1. The motorised drive unit would need to include a step-down mechanism to slow the normal operating output of the battery driven electric motor down from a continuous rate of 30–60 cycles per second to approximately one cycle every 1–5 seconds (2–3 seconds is preferred).

Figure 7:
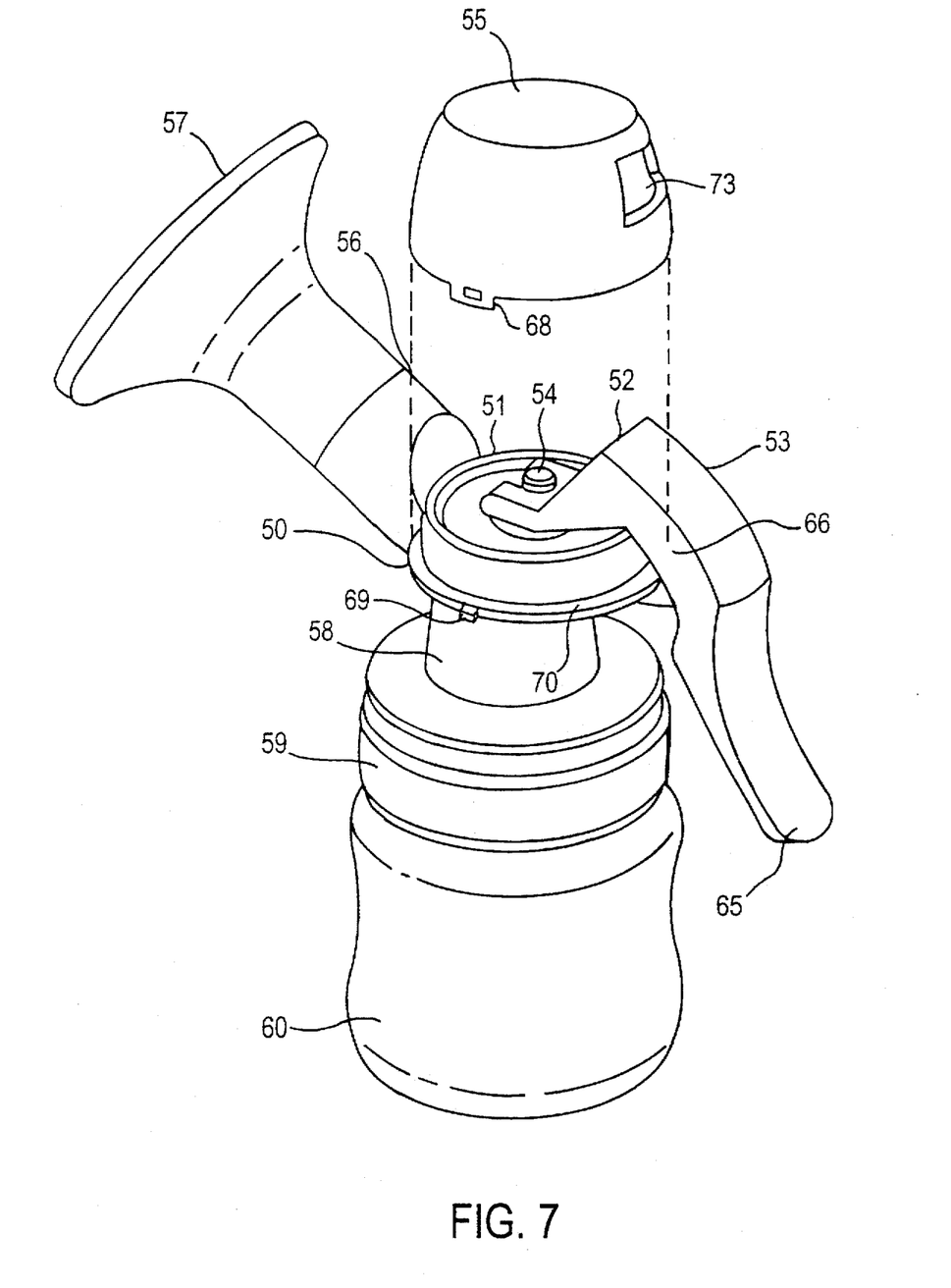
FIG. 7 is a perspective view of a second pump of the invention.

A second embodiment of the invention will now be described with reference to FIGS. 7 and 8. FIG. 7 illustrates a single handed breast pump comprising a moulded plastic body 50 with a diaphragm 51 mounted thereon at its upper end. A pivotally mounted lever 53 having a nose portion 52 is attached to a connector 54 protruding from a central hole 51a in the diaphragm 51. A cap 55 encloses the diaphragm 51 and the nose portion of fork 52 of lever 53.

The body 50 has an inlet 56 with a conical attachment 57 fitted thereto to receive the user's breast and nipple. The body is releasably connected to an adaptor 58 which receives a screw cap 59 to enable it to be screwed into collecting vessel 60.

The pump shown in FIGS. 7 and 8 will now be described in more detail. The upper region of the body 50 is formed with an annular shoulder 61 over which a rolled over annular lip 62 of the diaphragm 51 is fitted. The diaphragm 51 is made from a resiliently deformable material such as silicone rubber and has a central hole 51a therethrough in which a moulded plastics connector 54 is fitted. The diaphragm 51 is mounted in a lower annular rebate 54a formed at the base of the connector 54 which also includes an upper annular rebate 63 which receives and locates slotted end 64 of the nose portion 52 of the moulded plastics lever 53. The moulded plastics lever 53 also includes an operating hand portion 65 pivotally mounted on pivot 66 formed on the end of a support arm 67 extending laterally from the body 50 and integrally formed therewith. The support 67 is offset with respect to the longitudinal axis of the body 50.

The moulded plastics cap 55 is attached to the body 50 by means of a pair of diametrically opposed downwardly extending clip 68 (see FIG. 7) formed on its lower edge which engages with and receive diametrically opposed tabs 69 formed on outwardly projecting rim 70 of the body 50 (see FIG. 7). The lower internal annular face 71 of cap 55 is shaped to make a seal with the external face of the annular lip 62 of the diaphragm 51 to firmly retain and press against the annular shoulder 61 of the body 50 and create a fluid tight seal between the diaphragm 51 and the body 50. The cap 55 is also formed with an access opening 73 to enable the handle portion 65 of the lever 53 to protrude through the cap 55 to allow operation thereof. The body 50 has a tubular lower part 74 with a screw thread 75 thereon which cooperates with screw threads 74a formed on the inside wall of the upper end of a tubular adaptor 58 in known manner thereby providing a releasable connection between the body 50 and the adaptor 58. A releasable bayonet type connection could however be used. The diameter of the upper end of the adaptor 58 is less than that of hole 76 formed in the top surface of moulded plastic screw cap 59. The cap 59 fits over the upper end of the adaptor 58 and rests on an annular flange 77 protruding outwardly from the body of the adaptor 58. The plastic screw cap 59 has threads formed on the internal surface thereof so that the adaptor 58 and body 50 can be connected to a collecting vessel 60 (see FIG. 8) such as a baby feed bottle or other suitable container.

The body 50 also includes an internal dividing wall 78 which separates the body 50 from its lower part 74 and is formed with a central hole in which a button valve 50 is mounted. The valve 80 comprises spaced end portions 81 and 82 connected by a central core 83 whose length is greater than the thickness of the internal dividing wall 78 and of a diameter less than that of the central hole in it so that the valve 80 can move axially in the hole 79 by an amount equal to the distance separating the end portions 81 and 82.

The body 50 has a tubular inlet opening 56 extending laterally from one side and its open end is adapted to receive a conical trumpet 57 made of a rigid plastics material which is shaped to receive the breast and nipple of a user. The inlet 56 communicates with an inlet opening 84 formed in the body 50 to allow the passage of milk from the conical trumpet 57 through the inlet 56 and into the body 50. A soft resilient breast cushion of known type can be inserted in the trumpet 57 for increased comfort. Alternatively, a flexible moulded insert of the type described in our pending patent application Ser. No. 9502995.5 can be fitted in the trumpet 57 to additionally stimulate the nipple and encourage lactation.

Figure 8:
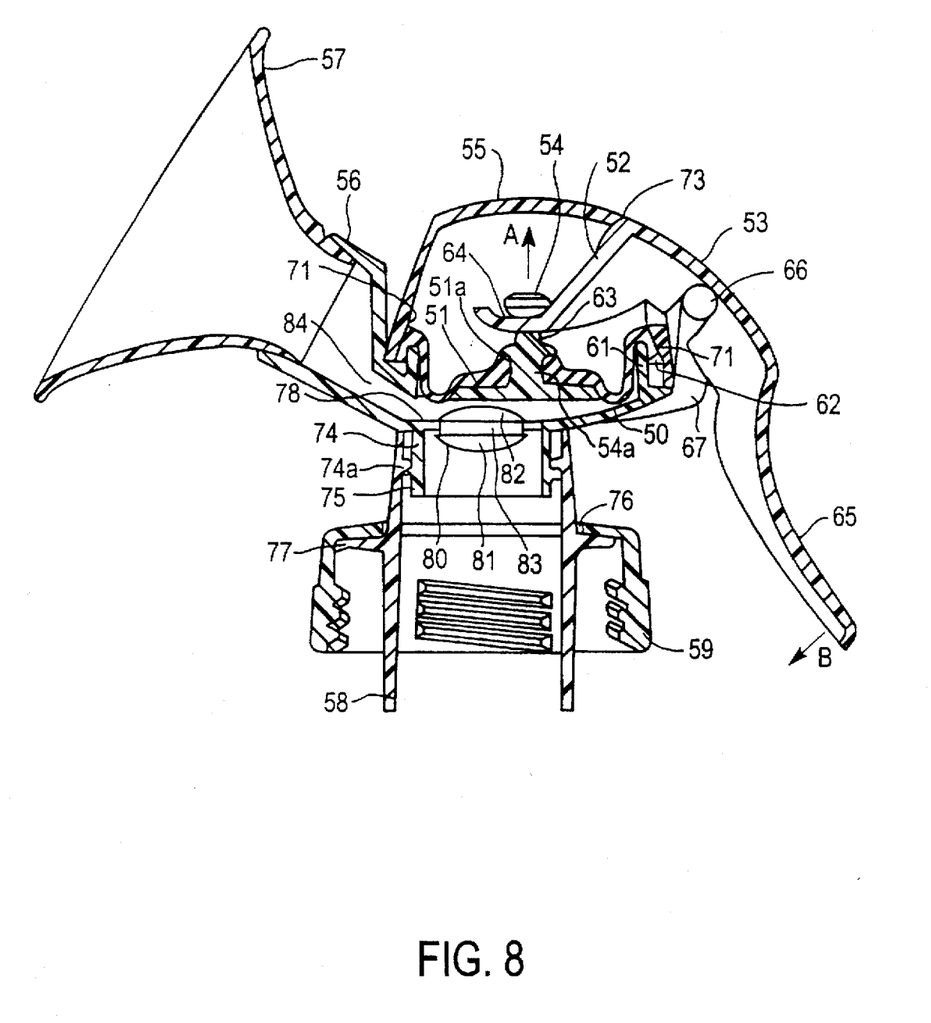
FIG. 8 is a cross section of the pump shown in FIG. 7 but omitting the milk collecting container.

The use and operation of the assembled breast pump illustrated in FIGS. 7 and 8 is as follows.

The user first inserts her breast and nipple into the open end of the conical attachment 57 and with one hand holds the body 50 and milk connecting vessel connected thereto against her breast. The fingers of the same hand can then be used to apply pressure to the handle portion 65 of lever 53 to move it in the direction of arrow B. This results in the handle portion 65 pivoting about the pivot 66 on the end of the support arm 67 thereby raising the nose 52 of lever 53 and lifting the connector 54 in the direction indicated by arrow A (see FIG. 8). This movement distorts the diaphragm 51 connected thereto upwardly and thereby creates a vacuum or negative pressure within the upper part of the body 50 above the button valve 80 which is immediately lifted upwardly causing it to seat against the lower face of the dividing wall 78 and form a seal therewith thus maintaining a negative pressure within the body 50. This negative pressure created within the body 50 between the valve 80, the underside of the diaphragm 51 and the users breast is sufficient to cause the breast to lactate and milk to be expressed therefrom. When the handle portion 65 of lever 53 is released, the resilience of the diaphragm material causes it to return to its original position causing the connector 54 and the nose 52 of lever 53 to drop. The negative pressure is thereby released and the valve 80 breaks its seal with the lower face of the internal dividing wall 78 thus allowing the expressed milk to fall under gravity through the opening therein and into the vessel 60.

The operation is then repeated in a cyclic fashion so as to create an alternating negative pressure in the nipple region which promotes lactation. It will be appreciated that this is achieved on each complete stroke of the lever 53 at a rate of between 1–5 cycles per second (2–3 is preferred) which is usually sufficient to promote lactation.

It will be appreciated that an advantage of the illustrated breast pump is the ease by which it may be assembled and disassembled to enable it to be properly sterilized before use. The way in which the breast pump shown in FIGS. 7 and 8 is assembled is as follows.

The moulded plastics connector 54 is first inserted through the central hole 51a in the diaphragm 51 so that the diaphragm locates in the lower annular rebate 54a of the connector 54. The diaphragm 51 with the connector 54 fitted thereto is then lowered onto the body 50 until the lip 62 of the diaphragm 51 engages with the annular shoulder 61 of body 50. The cap 55 is then lowered into position over the annular lip 62 of diaphragm 51 and annular shoulder 61 until its internal face 71 engages the annular lip 62 of diaphragm 51 and pushes it against the annular shoulder 61 of body 50 to form a fluidtight seal therewith. The clips 68 on cap 55 are then engaged with the tabs 69 on the body 50 to retain it in position thereon. The operating part 52 of lever 53 is then inserted through the hole 73 in cap 55, and the slot 64 in the nose portion 52 of lever 53 is engaged with the upper annular rebate 63 beneath the enlarged head on the stem connector 54. The lever 53 is then mounted oil the pivot 66 on the end of the support arm 67. The correct size adaptor 58 is now chosen depending on the size of the milk collecting vessel 60 to which it is to be fitted and this is attached to the body 50 by means of the releasable connection 74a,75 having first placed the screw cap 59 over the upper end of the adaptor 58 so that it rests against the outwardly extending annular flange 77 formed on the body of adaptor 58. The lower part of the adaptor 58 is then inserted onto the vessel 60 and the screw cap 59 is screwed onto the vessel 60. The pump is now ready to use. In order to disassemble the breast pump the above steps are carried out in reverse.

It will be appreciated that the manually operated pump just described with reference to FIGS. 7 and 8 could be readily modified to be electrically driven by simply replacing the lever 65 with one of a different design which can be attached to the output end of a motorised drive unit which includes a speed reducing mechanism (not shown), the motor being mounted with batteries in a housing which can be attached to the body 50. The speed reducing mechanism reduces the normal continuous output from the motor from between 30–60 cycles per second to a rate of one cycle every 1–5 seconds (2–3 seconds is preferred).

It should be noted that in some circumstances, it may be desirable to fit a flexible moulded insert in the inlet trumpet 8 or 57 for instance as described in our pending patent application Ser. No. 9502995.5 to provide additional stimulation in the nipple area and thereby improve lactation.

Whilst the diaphragm in the preferred embodiments just described is cup-shaped, it is envisaged within the scope of the invention that a flat disc shaped diaphragm of any suitable shape could be used whose edge regions are mounted in the body 1. For instance, the body could have an annular rebate formed therein to receive the edge of the diaphragm and this could be held in position by a cooperating part on a cover or top portion of the body which screws onto the body or is attached thereto in some other way. The diaphragm could however be stuck in the body, glued in or screwed in. It could even be moulded as an integral part of the body.

We claim:

1. A breast pump comprising:
   a body, said body having an inlet;
   a breast receiving portion connected to the inlet and shaped to receive a portion of a user's breast and nipple;
   means for releasably connecting an expressed milk collecting container to said body;
   a deformable diaphragm disposed in the body;
   actuating means operatively connected to the diaphragm for cyclicly moving said diaphragm to generate a negative pressure in the inlet; and
   valve means mounted in the body for cyclically releasing the negative pressure which is generated in the inlet.

2. A pump as claimed in claim 1, wherein the actuating means are connected directly to the diaphragm.

3. A pump as claimed in claim 1, wherein the diaphragm has a connector extending upwardly therefrom and the actuating means are releasably attached thereto.

4. A pump as claimed in claim 3, wherein the connector is integrally formed with the diaphragm.

5. A pump as claimed in claim 3, wherein the connector is a separate member releasably attached to the diaphragm.

6. A pump as claimed in claim 1, wherein the diaphragm is cup-shaped, a retaining member releasably retaining the diaphragm in the body to make a fluid tight seal therewith.

7. A pump as claimed in claim 6, wherein the body is formed with an upstanding annular lip, and an annular rebate formed around the circumference of the diaphragm, said annular rebate and the retaining member holding the diaphragm in sealing engagement therewith.

8. A pump as claimed in claim 6, wherein the retaining member is a cover with an annular sealing surface, said cover fitting on the top of the body to enclose the diaphragm whereby the annular sealing surface engages an outer surface of the diaphragm to hold it in sealing engagement with the annular lip on the body.

9. A pump as claimed in claim 8, wherein the cover includes retaining means to hold said cover in position on the body.

10. A pump as claimed in claim 6, wherein the retaining member includes a pivot support projecting therefrom on which the actuating means is pivotally mounted.

11. A pump as claimed in claim 6, wherein the actuating means is a lever with attachment means at one end thereof for releasably connecting said lever to the diaphragm.

12. A pump as claimed in claim 11, wherein a connector extends upwardly from the diaphragm and wherein the attachment means comprises a forked end on the lever which engages with said connector.

13. A pump as claimed in claim 12, wherein the connector includes an enlarged head portion which is provided at one end thereof and which is engaged by said forked end of the lever.

14. A pump as claimed in claim 12, wherein the lever is moved against the resilience of the diaphragm.

15. A pump as claimed in claim 1, wherein the actuating means is a lever.

16. A pump as claimed in claim 15, wherein the lever is pivotally mounted on the body for single handed operating by the user.

17. A pump as claimed in claim 15, wherein the lever is pivotally mounted for movement relative to the body in a direction generally normal thereto.

18. A pump as claimed in claim 1, wherein the valve means comprises a plug valve fitted in an aperture in a wall extending across the body.

19. A pump as claimed in claim 1, wherein said releasably connecting means includes an adaptor and wherein the pump body and the adaptor have cooperating releasable connection means.

20. A pump as claimed in claim 1, wherein the actuating means is driven by a motorized drive unit including an electric motor.

21. A pump as claimed in claim 20, including a speed reducing mechanism operable to reduce the normal continuous operating cycle of the electric motor from 30–60 cycles per second to one cycle per 1–5 seconds.

* * * * *